(12) United States Patent
Dudasik

(10) Patent No.: US 6,648,893 B2
(45) Date of Patent: Nov. 18, 2003

(54) FACET FIXATION DEVICES

(75) Inventor: Michael Dudasik, Nutley, NJ (US)

(73) Assignee: Blackstone Medical, Inc., Springfield, MA (US)

( * ) Notice: Subject to any disclaimer, the term of this patent is extended or adjusted under 35 U.S.C. 154(b) by 0 days.

(21) Appl. No.: 09/837,624

(22) Filed: Apr. 18, 2001

(65) Prior Publication Data

US 2003/0032960 A1 Feb. 13, 2003

Related U.S. Application Data

(60) Provisional application No. 60/243,920, filed on Oct. 27, 2000.

(51) Int. Cl.$^7$ ............................................. A61B 17/56
(52) U.S. Cl. ....................................................... 606/73
(58) Field of Search ............................... 606/73, 72, 63, 606/66, 68

(56) References Cited

U.S. PATENT DOCUMENTS

| | | | | | |
|---|---|---|---|---|---|
| 2,490,364 A | * | 12/1949 | Livingston | ................... | 606/68 |
| 4,590,928 A | * | 5/1986 | Hunt et al. | ................... | 606/72 |
| 4,711,234 A | * | 12/1987 | Vives et al. | ................... | 606/60 |
| 5,601,558 A | * | 2/1997 | Torrie et al. | ................... | 606/72 |
| 5,702,397 A | * | 12/1997 | Goble et al. | ................... | 606/72 |
| 5,713,903 A | * | 2/1998 | Sander et al. | ................... | 606/72 |
| 5,720,753 A | * | 2/1998 | Sander et al. | ................ | 606/104 |
| 5,782,865 A | * | 7/1998 | Grotz | ......................... | 606/232 |
| 6,406,479 B1 | * | 6/2002 | Justin et al. | ................ | 606/104 |

* cited by examiner

Primary Examiner—Eduardo C. Robert
(74) Attorney, Agent, or Firm—Greenberg Traurig LLP

(57) ABSTRACT

The present invention is an expandable sleeve deployable in a surgical implant. The sleeve has a head, a tubular shaft defining an open interior, and a distal tip, with the shaft having a length dimension. The shaft is provided with a plurality of slots that divide the shaft into partitions, wherein each of the partitions has a length, and the length of the partitions are not all equal. For example, the slots may have a curved portion that extends at an angle between 0° and 90° to the length dimension of the shaft. The slots may also have a straight portion and a curved portion. Further, the invention in another embodiment includes an expander pin, and in yet another embodiment, includes an expander pin.

38 Claims, 10 Drawing Sheets

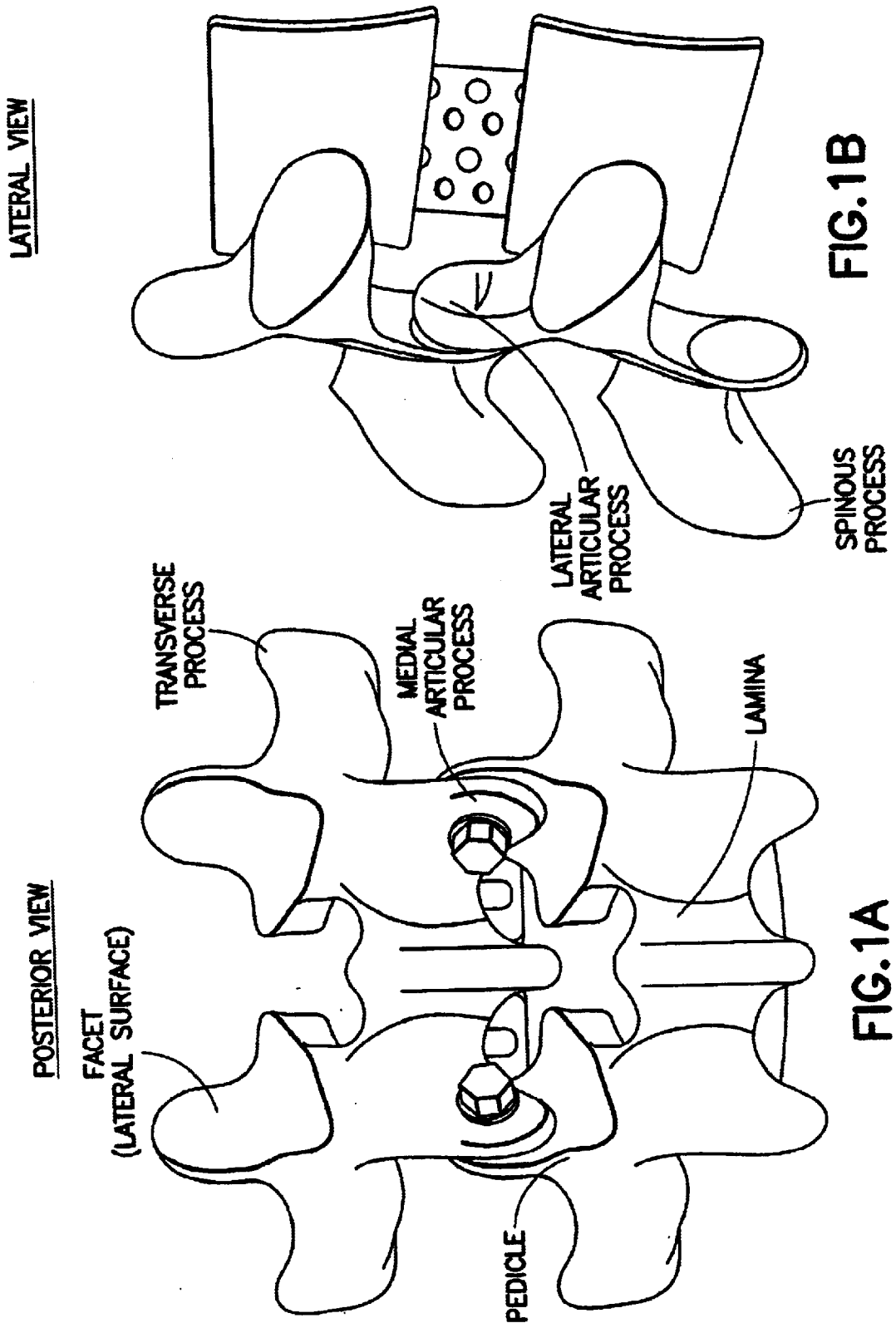

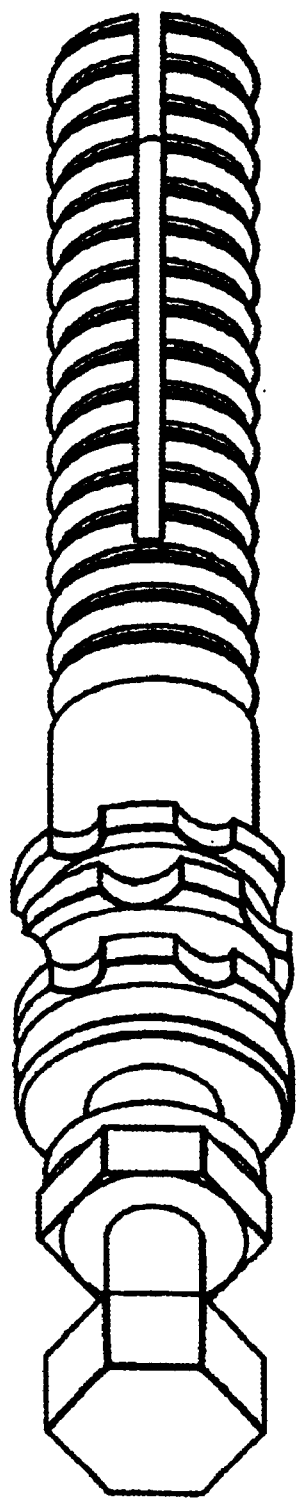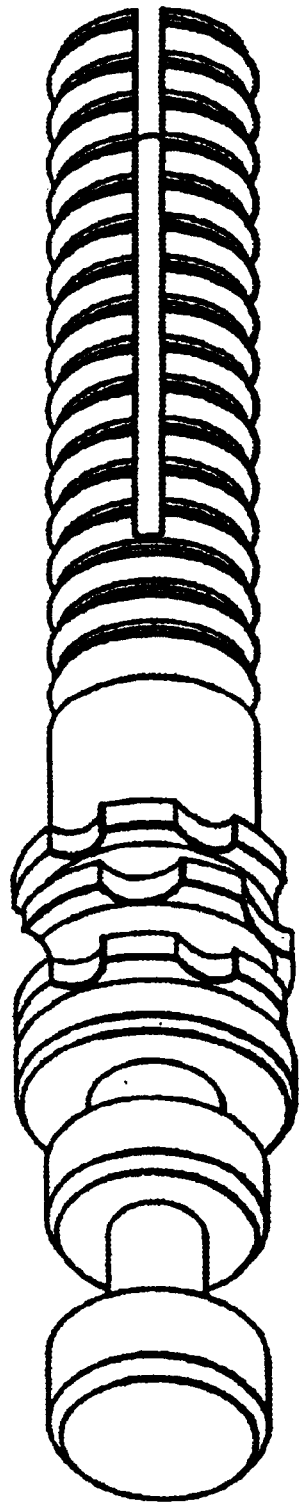

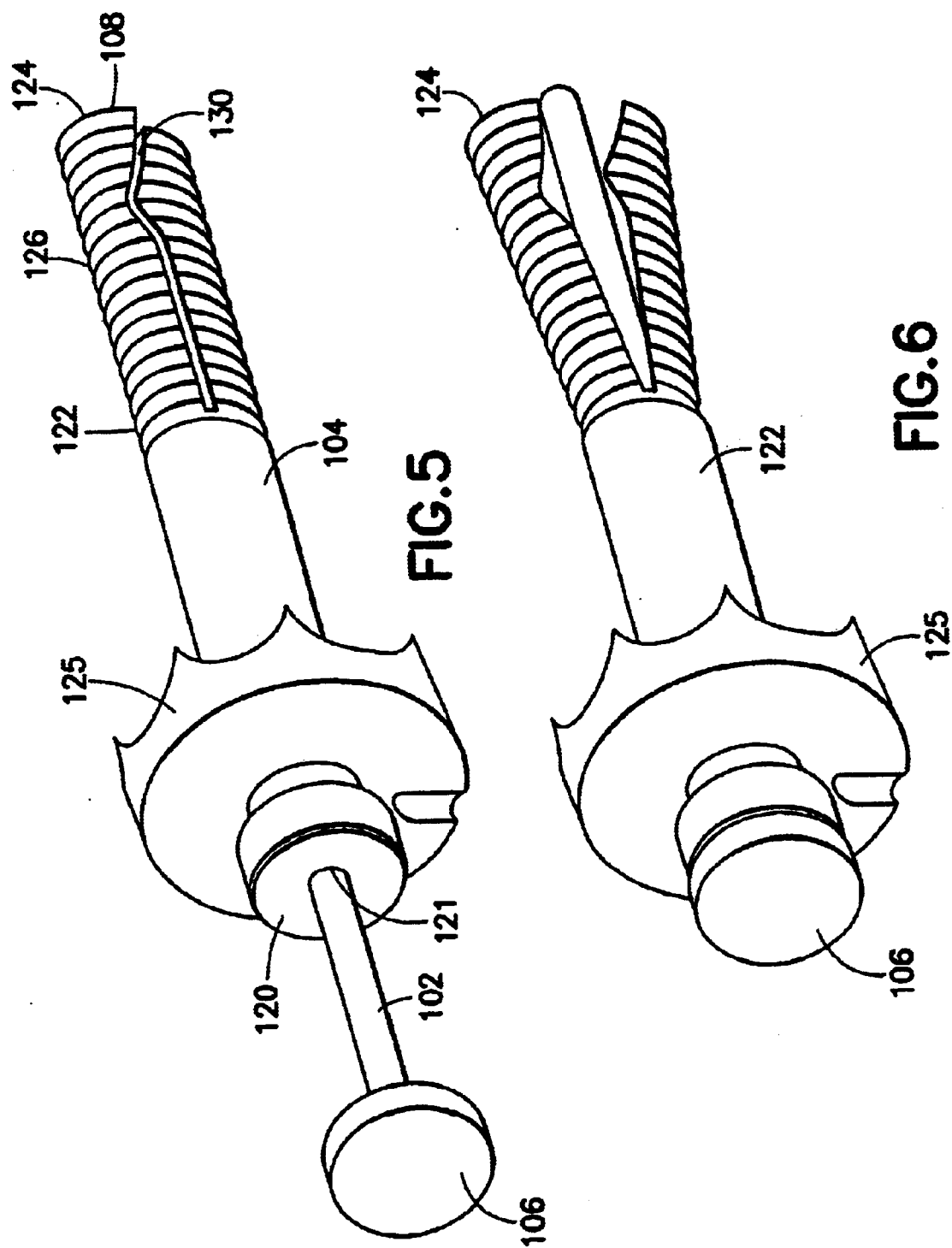

FACET FIXATION DEVICES

STATEMENT OF RELATED CASES

The present application claims the benefit of U.S. provisional application No. 60/243,920 filed on Oct. 27, 2000.

FIELD OF THE INVENTION

The present invention is directed to devices that are used to facilitate post-operative bone-to-bone fusion, tissue-to-bone fusion and particularly, bone fusion between two adjacent vertebrae.

BACKGROUND OF THE INVENTION

Vertebral disc degeneration has been associated with back pain and motor function loss. Loss of disc space height, extrusion of disc material, and translation of the vertebrae can result in compression of the spinal cord and nerve roots. One prescriptive treatment is to stabilize the vertebral bodies through fusion of adjacent vertebrae within the spinal column.

An operative technique of spinal column fusion employs inter-vertebral body cages. Available in different configurations from several manufacturers, the cage is inserted between two vertebral bodies in order to restore space between the discs. The device is filled with bone graft to promote fusion between the vertebrae. Access holes around the periphery of the cage provide intimate contact between the graft and host bone. The cages are typically inserted from the back (posterior) or front (anterior) aspects of the spinal column. The anterior approach involves laparoscopic methods.

Stabilization of the fusion site is advantageous in the early post-operation period. Similar to fracture healing, new bone is overlayed between the vertebral bodies, using the graft material as a lattice. Using cages as stand alone devices has met with limited success for the reason that immediate stabilization is not always guaranteed. For this reason, supplemental fixation is becoming more commonplace.

One current stabilization technique employs the placement of fixed translaminar screws into a hole drilled through adjacent vertebrae. FIGS. 1A and 1B show typical lumbar vertebrae in which translaminar screws are driven across the facet joint, effectively locking the two vertebrae in place while allowing for the four types of spine motion: forward flexion, backwards extension, axial torsion, and lateral flexion.

There is an ongoing need to provide for a facet fixation device that can be delivered simply, accurately, and quickly, while providing performance that is superior or equal to that of screw fixation.

SUMMARY OF THE INVENTION

In one aspect, the present invention is an expandable sleeve deployable in a surgical implant. The sleeve has a head, a tubular shaft defining an open interior, and a distal tip, with the shaft having a length dimension. The shaft is provided with a plurality of slots that divide the shaft into partitions, wherein each of the partitions has a length, and the length of the partitions are not all equal. For example, the slots may have a curved portion that extends at an angle between 0° and 90° to the length dimension of the shaft. The slots may also have a straight portion and a curved portion.

In yet another embodiment, the expandable sleeve has an open interior that is provided with a first zone proximate the head which has a first cross sectional area and a second zone proximate the distal tip that has a second cross sectional area, wherein the first cross sectional area is greater than the second cross sectional area. In yet another embodiment, the expandable sleeve has a third zone positioned intermediate the first zone and second zone, the third zone having a varying cross sectional area that decreases incrementally moving from the first zone to the second zone.

In yet another embodiment, the slots of the expandable sleeve extend from a midsection of the shaft to a terminal location on the shaft that is short of the distal tip. In another embodiment, the head extends outward from the shaft and is provided with teeth facing the distal tip. In yet another embodiment, the head of the expander pin extends outward from the shaft and has a convex distal tip.

In yet another embodiment, the head of the expandable sleeve is provided with a recess for receiving a bushing. The recess may be provided with a tapered profile that varies in cross sectional area over a length dimension.

In yet another embodiment, the slots divide the shaft into a first slot half and a second slot half, with the length dimension of the first half being greater than the length dimension of the second half. In yet another embodiment, the shaft of the expandable sleeve is provided with additional slots that divide the shaft into four quarters, wherein the length dimension of two quarters is greater than the length dimension of the two other quarters.

In yet another embodiment, the shaft of the expandable sleeve is provided with fenestrations on an exterior side. The fenestrations may vary in their length as measured in a radial dimension of the sleeve.

In yet another embodiment the present invention is a surgical implant having an expandable sleeve having any of the features as aforedescribed, and an expander pin comprised of a head and a shaft positioned within the open interior of the sleeve. The cross sectional area of the expander pin is larger than cross sectional area of at least a portion of the cross sectional area of the open interior, so that when the expandable pin is moved through the open interior, the expandable sleeve expands at the slots.

The expander pin has a distal tip and an end opposite the head, wherein the shaft is provided with a first zone proximate the head having a first cross sectional area and a second zone proximate the distal tip having a second cross sectional area, wherein the second cross sectional area is greater than the first cross sectional area.

In a further embodiment, the surgical implant is further provided with a bushing that resides in a cavity positioned within the open interior of the sleeve, located proximate the opening of the sleeve. The bushing has a shaped portion and a flange portion extending outward of the shaped portion, the bushing further provided with a through-channel dimensioned to receive the pin, and a discontinuation in the bushing, the channel being sized the same as or substantially the same as the pin, wherein the cavity is provided with dimensions complimentary to the dimensions of the shaped portion to retain the shaped portion within the sleeve. The shaped portion may have a tapered shape. The pin may be positioned within the sleeve by passing it through the bushing, which expands the bushing.

For simplicity's sake, as used herein the words "tube" or "tubular" are used with the intention of encompassing a hollow structure of any shape, whether cylindrical or not.

BRIEF DESCRIPTION OF THE DRAWINGS

FIGS. 1A, 1B shows a posterior and lateral view, respectively of prior art fixation devices.

FIGS. 4A–4B show alternatives to the FIGS. 2A–2C embodiments.

FIG. 5 shows a perspective view of another embodiment of the present invention in an unexpanded position.

FIG. 6 shows a perspective view of the embodiment of FIG. 5 of the present invention, this time in an expanded position.

DETAILED DESCRIPTION OF THE PREFERRED EMBODIMENT

Figure 2A:
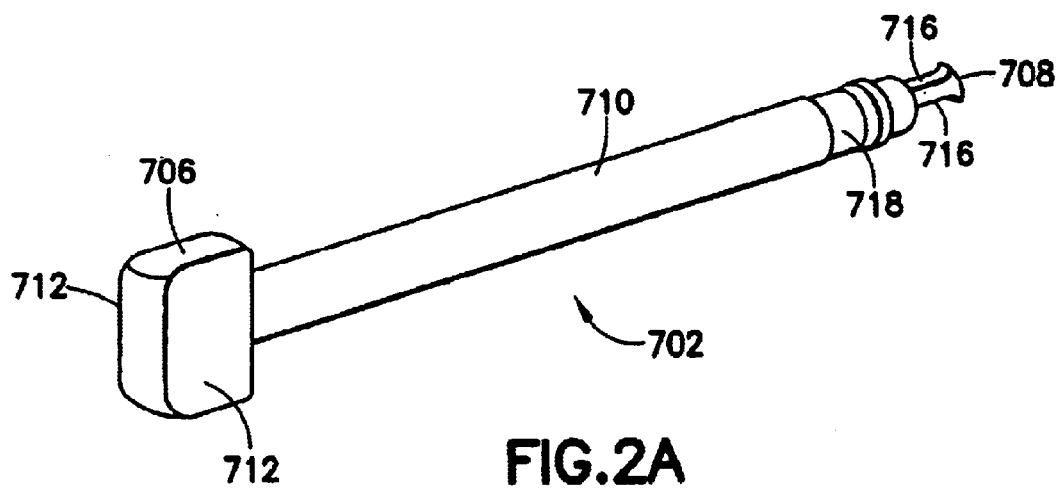
FIGS. 2A–2C show an earlier embodiment of the applicant surgical implant made subject of the aforedescribed provisional application.
Figure 2B:
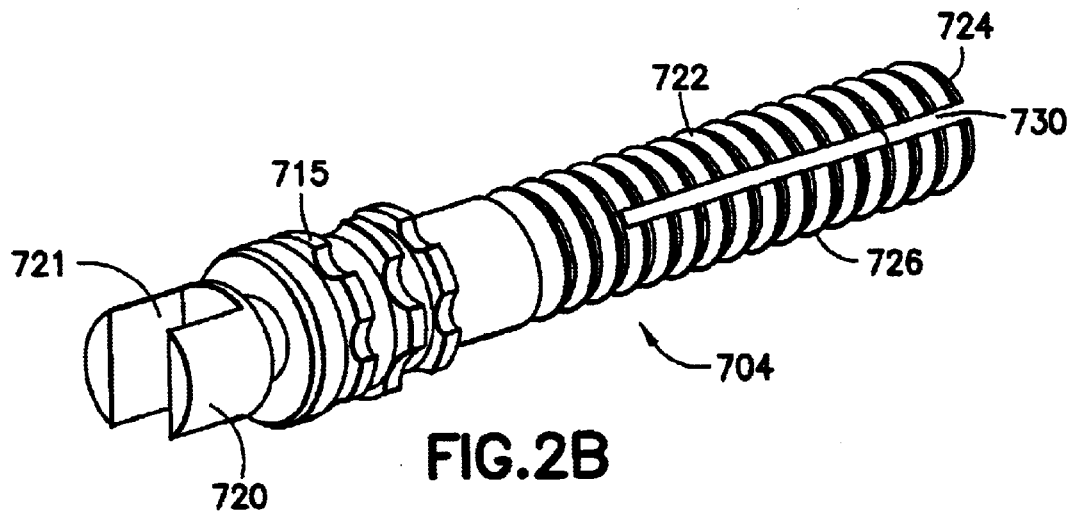
Figure 2C:
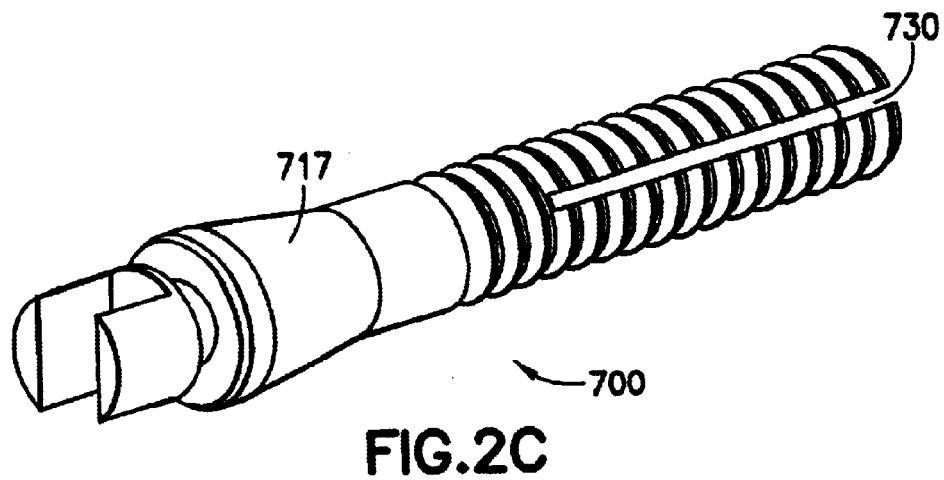

FIGS. 2A–2C shows a two piece fixation device 700 utilizing a pin 702 and a sleeve 704. The pin 702 (FIG. 2A) is comprised of a head 706 and a tip 708 which are connected by a cylindrical shaft 710. The head may be provided with flat sides 712. Due to the size of head 706, which is greater than the size of the opening in the sleeve into which the pin is inserted, the head eventually provides a positive stop when the pin 702 is driven into the sleeve 704.

Figure 3A:
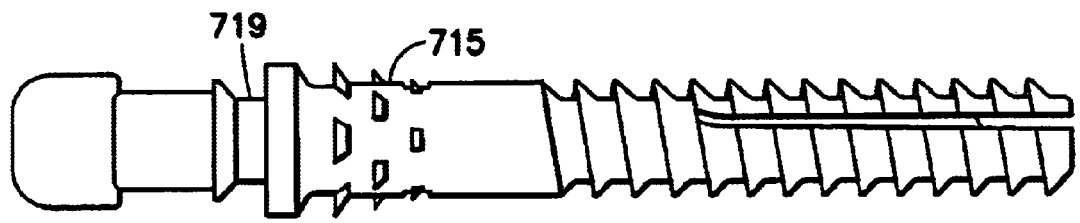
FIGS. 3A–3D show side plan and cross sectional views of the FIGS. 2A–2C surgical implant.
Figure 3B:
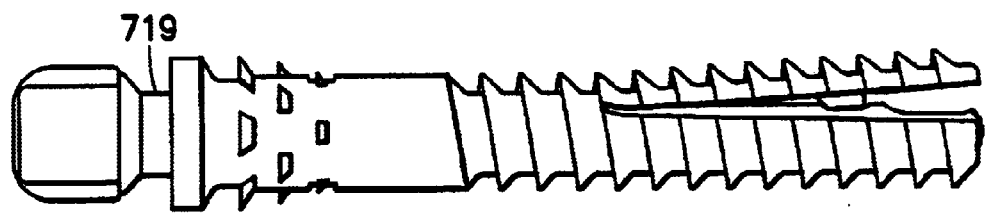
Figure 3C:
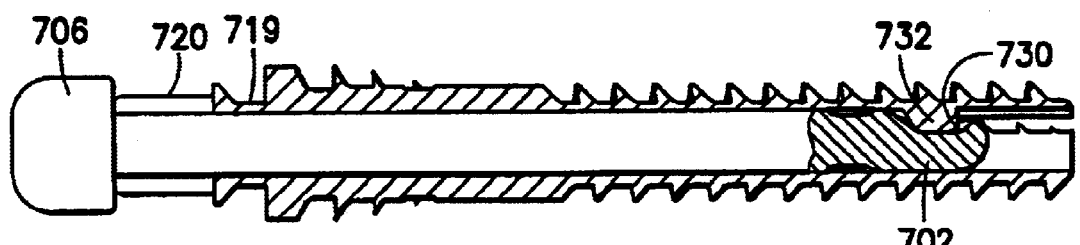
Figure 3D:
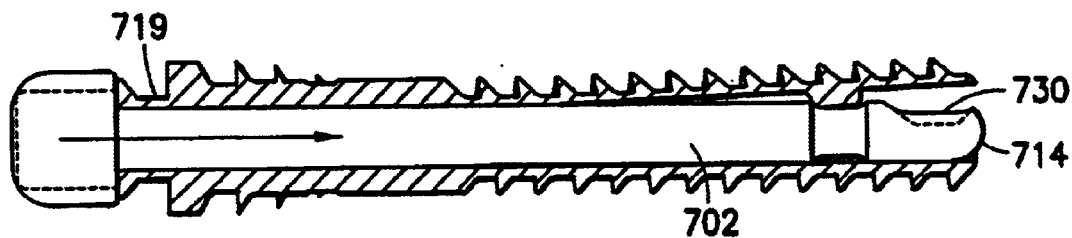

Tip 708 is provided with a rounded end 714 (FIGS. 3C, 3D) which facilitates the entry the expander pin 702 into the sleeve 704 and provides a smooth surface to reduce or avoid tissue irritation. Behind the spherical tip, in the direction of the shaft 710 is at least one recess 716. A plurality of recesses 716 are shown in FIG. 2A. The recesses are less thick when compared to the thickness of the shaft 710. Behind the recesses, also in the direction of the shaft 710, is an undercut 718, which also is a region of reduced thickness.

Sleeve 704 (FIG. 2B) is comprised of a head 720, a hollow tubular mid-shaft 722, and a distal tip 724. Head 720 has a slot 721 which receives the head 706 of the expander pin 702. Behind this is an undercut that captures an inserter instrument. One wall of the undercut is graduated to ease disengagement of the Inserter. The mid-shaft 722 has a series of fenestrations 726 intended to provide an interference fit with the walls of the hole prepared in the bone or tissue. The distal tip 728 has a series of slots 730 which allow the sleeve to expand.

The interior of sleeve 704 is open so that the pin 702 can be received therein. The inner wall of the sleeve 704 near the distal tip 728 is provided with tabs 732 that project into the open space. As the pin is driven the Tabs engage the undercut on the pin. The exterior of the distal tip has fenestrations 715 that in the deployed condition create an interference fit with the walls of the prepared hole. The distal tip may also be smooth. The fenestrations of the preferred embodiment resemble a cortical screw thread. They could however be of any configuration (grooves, splines, etc.) which would provide a "bite".

FIG. 2C shows a tapered portion 717 as an alternate to the fenestrations 715. Rather than cutting into bone, the taper would engage a conic shape prepared in the bone, providing a measure of resistance to pull out of the Implant.

FIGS. 3A, 3B, 3C, and 3D illustrate the transformation of the implant from the non-deployed, pre-expanded state to the deployed, expanded state. The sleeve and pin arrangement is inserted into the prepared drill hole in the initial, non-deployed state. In the initial, non-deployed state, in which the head 706 of the pin is situated outside of the slotted head 720 of the sleeve, the tab 732 on the inner wall of the sleeve resides within the slot 730 provided on the pin 702. In this arrangement the sleeve is in an unexpanded state. The pin 702 is then moved forward in the sleeve 704 so that the head 706 of the pin 702 is situated in the slot 721 of the head 720 on the sleeve 704. Forward movement of the pin moves the recess out from under tab, and the tab rides up on the shaft 710. Since the shaft is thicker than the recess, the abutment of the tab against the shaft expands the sleeve at the recessed region. To maintain the tab in position on the sleeve, the shaft is provided with an undercut, which is a grooved region on the shaft having a modest reduction in thickness, i.e., a thickness intermediate that of the recess 716 and shaft 710. The undercut 718 is situated where the tab will reside when the pin is fully inserted in the sleeve and the device is in the deployed state. The walls of the groove retain the tab within the undercut, insuring that the tab will remain within the groove. See, e.g., FIG. 25D.

FIGS. 4A and 4B show alternate head configurations. In these embodiments, the slotted head of the sleeve 704 is omitted and the head of the pin is replaced by a hex head (FIG. 4A), or alternatively by a smooth head (FIG. 4B).

Figure 7:
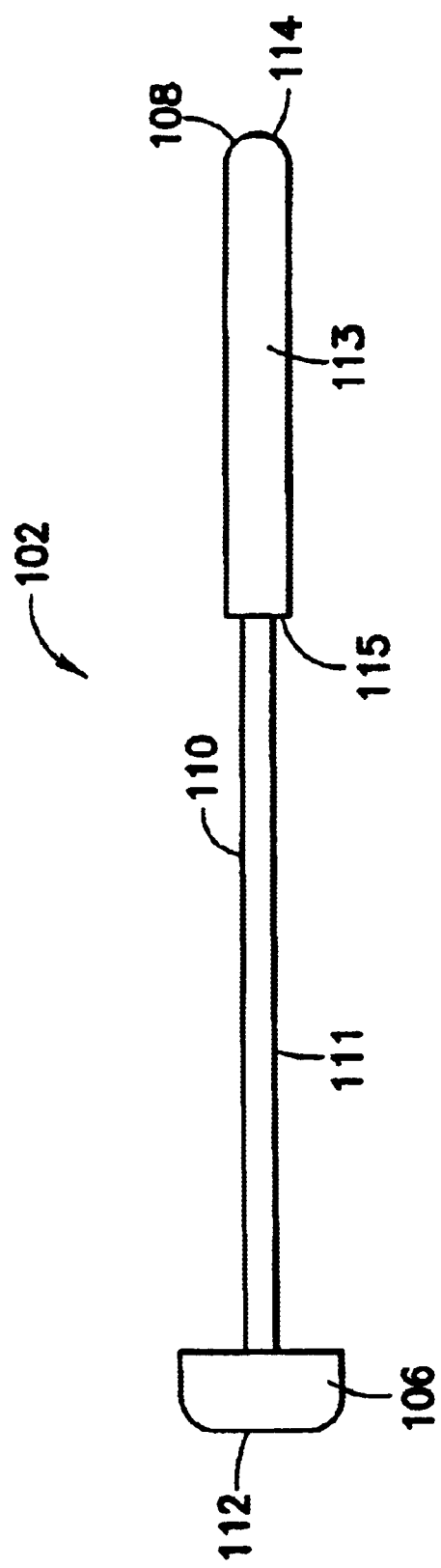
FIG. 7 shows an embodiment of an expander pin.

FIGS. 5 and 6 show a two piece fixation device 100 utilizing a pin 102 and a sleeve 104. As best seen in FIG. 7 the pin 102 has a head 106 and a cylindrical shaft 110 having a tip 108. As shown in FIG. 7, the shaft is provided with a midsection 111 and distal end 113. Distal end 113 is sized greater than the midsection 111. The increase in size may take place stepwise at step 115. The head 106 may be provided with a rounded perimeter 112. Due to the size of the head 106, which is greater than the size of the opening 121 in the sleeve into which the pin is inserted, the head provides a positive stop when the pin 102 is driven into the sleeve 104. See FIGS. 6 and 9.

Tip 108 is provided with a rounded surface 114 at distal end 113 which facilitates entry of the pin 102 into the sleeve 104 and provides a smooth surface to reduce or avoid tissue irritation distal end 113. See FIGS. 7, 8, 9.

Figure 15:
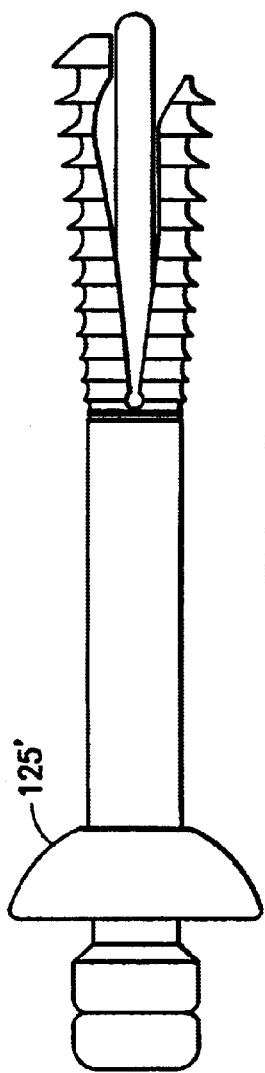
FIG. 15 is a side elevational view of another embodiment of the present invention.
Figure 16:
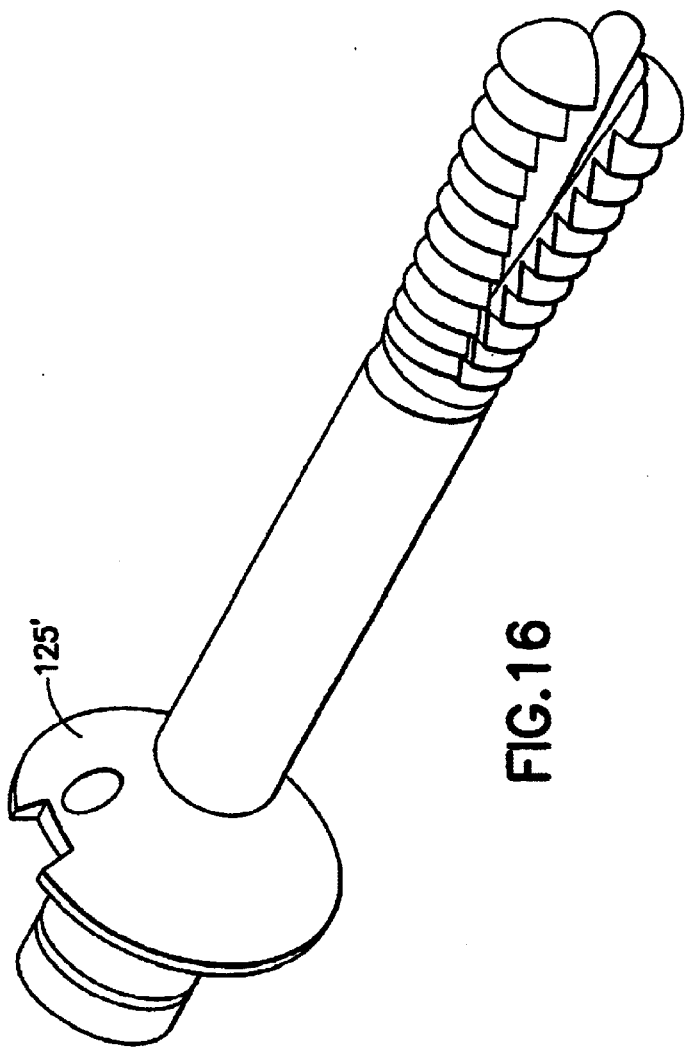
FIG. 16 is a perspective view of another embodiment of the present invention.

Sleeve 104 (FIG. 5) is provided with a head 120 having an opening 121. A shaft 122 extends from the head 120. The shaft 122 defines an open interior which can be accessed through the opening in the head 120. The pin 102 can be inserted through the opening and is received in the open interior. The shaft 122 is also provided with slots 130 that extend from the mid-section of the shaft 122 to the distal tip 124. The sleeve 102 is also provided with a flange 125 to resist forces that would pull the device through the bone. The flange 125 may be provided with a plurality of teeth 129 directed distally, for additional fixation. The flange 125 is provided with a convex shape to better engage the bone. In an alternative embodiment illustrated in FIGS. 15 and 16, the flange 125' is provided with a smooth, curved distal facing side that extends radially outward from the sleeve 102. This arrangement may better conform to the host bone. The flange may be hemispherical in shape.

Figure 11:
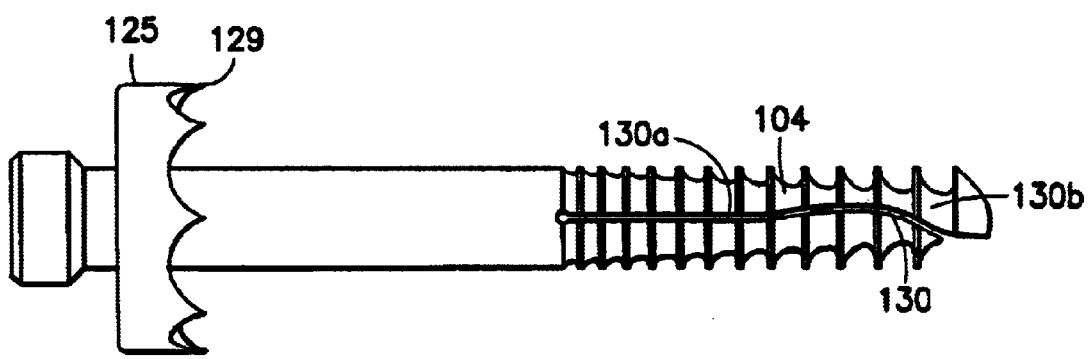
FIG. 11 is a side elevational view of the sleeve of the present invention.
Figure 12:
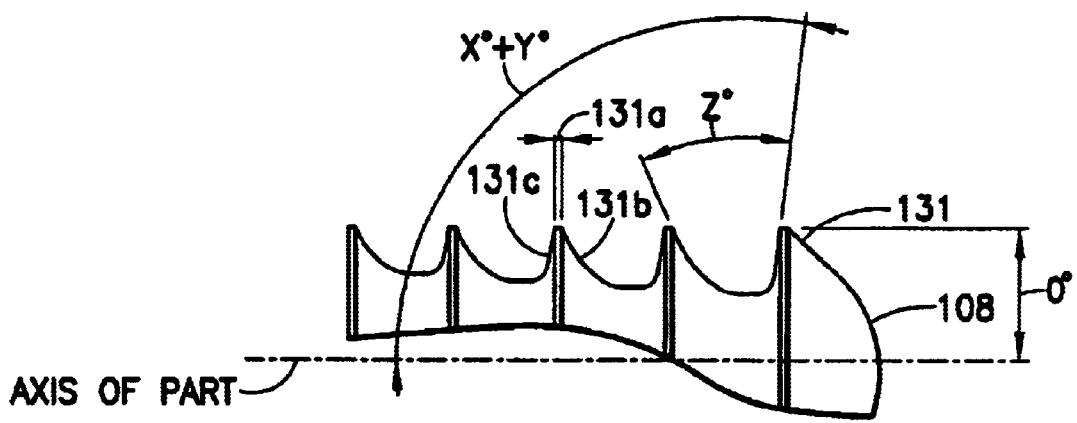
FIG. 12 is a side elevational view of a half of the distal tip of the sleeve of the present invention.
Figure 13:
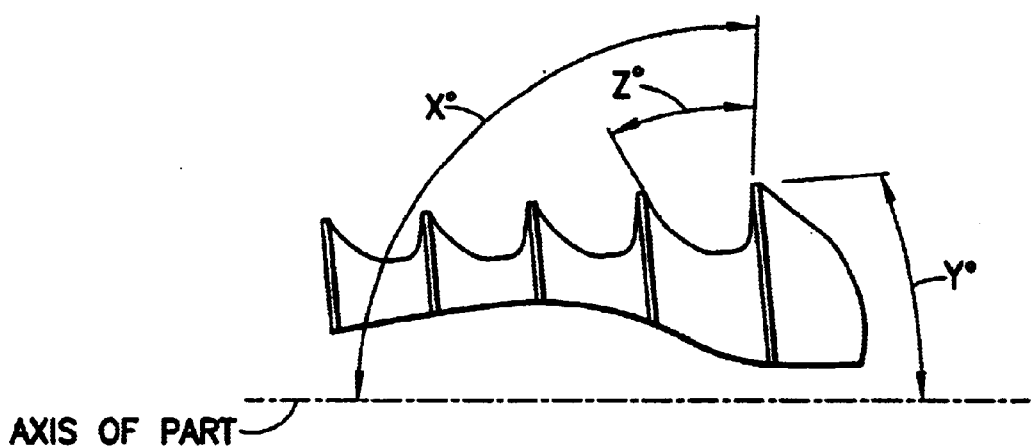
FIG. 13 is a side elevational view of a half of the distal tip of the sleeve of the present invention.
Figure 14:
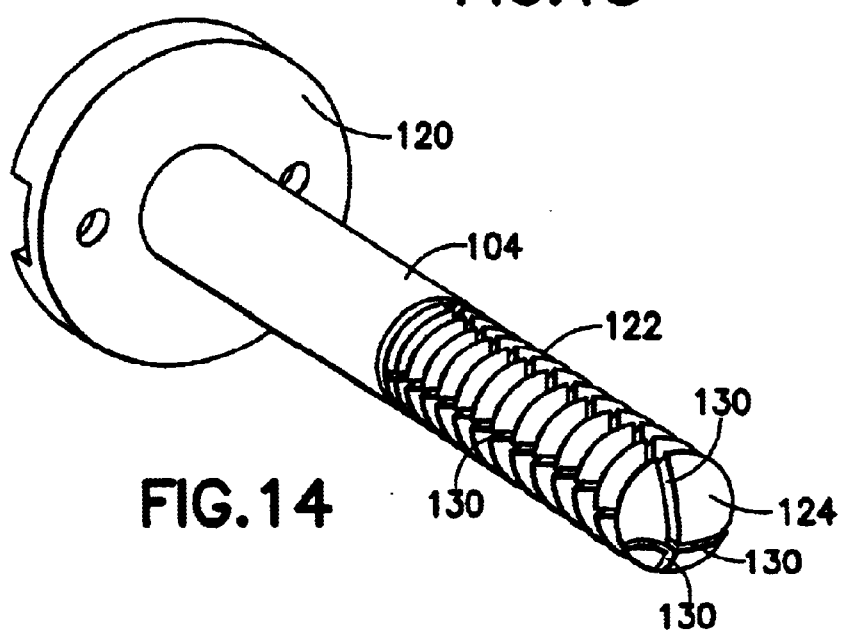
FIG. 14 is a perspective view of another embodiment of the present invention.

The outer side of the shaft 122 has a series of fenestrations 126 intended to provide an interference fit with the walls of the hole prepared in the bone or tissue. As best seen in FIGS. 11–13, the fenestrations 126 have a variable root diameter, which is the outer shaft diameter minus the diameter of the grooves of the fenestrations. See FIG. 12. Root diameter decreases as the tip 108 is approached. This places the largest and deepest fenestrations near the distal end 113, which is the location of the greatest sleeve expansion. This arrangement may maximize interference with the bone. The fenestrations 126 with a shallow depth are located near the midsection, a location where sleeve wall thickness is maximized for strength. In one embodiment, the fenestrations 126 can be a series of circumferential grooves. In another embodiment the fenestrations take the form of a single lead thread, of varying pitch and minor diameter. Thread pitch decreases as the distal tip 108 is approached. Minor diameter decreases as the distal tip 108 is approached.

The profile of a Fenestration 131 consists of a crest width 131a, a clearance flank 131b, and a pressure flank 131c. These are based on standards set forth in ASTM F 543-98: *Standard Specification for Metallic Metal Bone Screws*. In FIG. 12, the angles X and Z are given in the standard. To match these in the deployed state, the entire profile is tilted Y degrees, yielding an angle from horizontal of X+Y degrees to the pressure flank. This will mimic the interference pattern of the standard.

Figure 8:
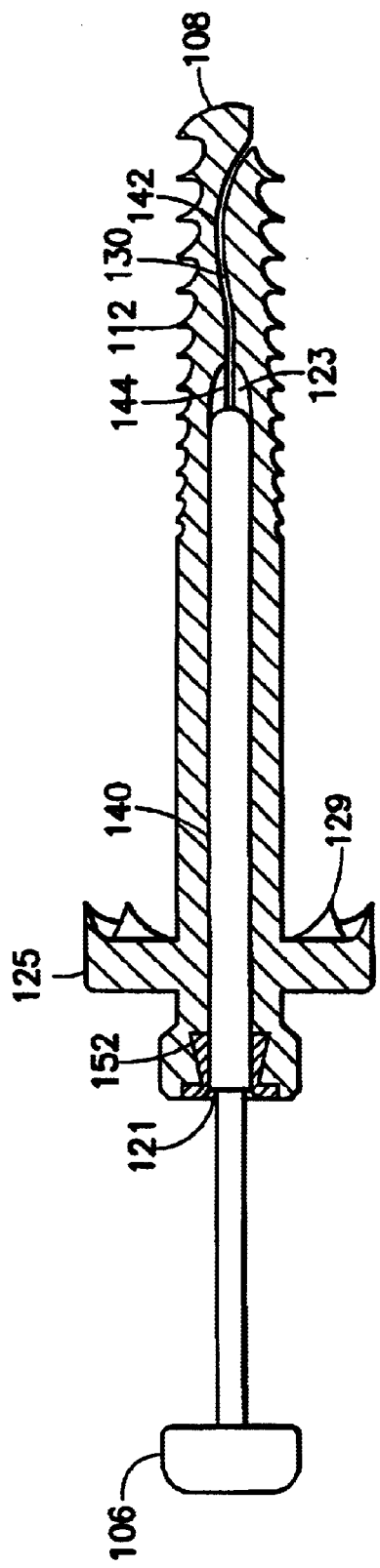
FIG. 8 is a cross sectional view of the embodiment of FIG. 5 of the present invention in which the sleeve is in an unexpanded state.
Figure 9:
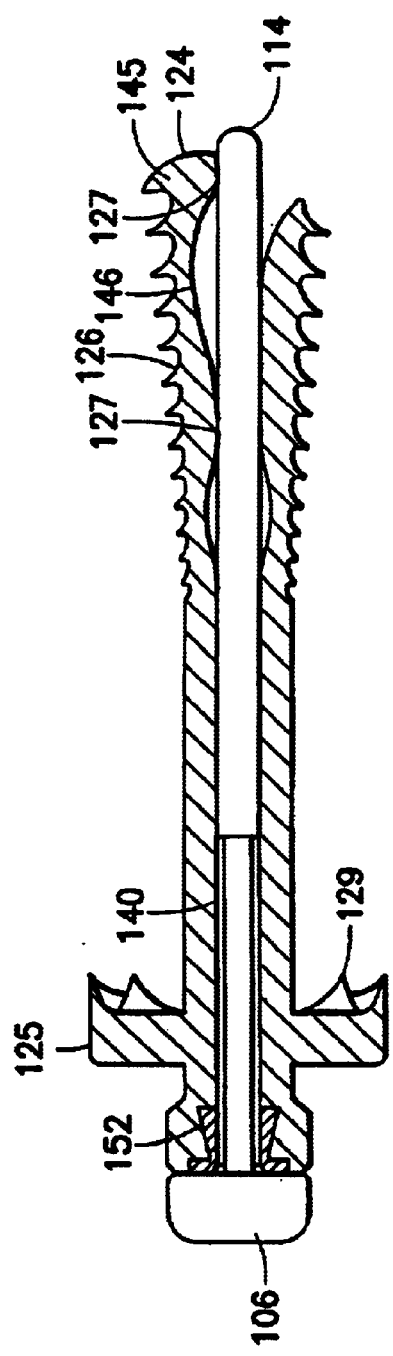
FIG. 9 is a cross sectional view of the embodiment of FIG. 5 of the present invention in which the sleeve is in an expanded state.

The slot 130 in the sleeve 104 runs from the midsection of the shaft 122 to near the distal tip 108. The slot 130 extends through the sidewalls of the sleeve 104, from the exterior of the sleeve to the open interior defined by the sleeve. The slots divide the sleeve 104 into partitions. In FIGS. 8, 9, and 12, two slots are shown, dividing the sleeve into halves. The path of the slot is substantially aligned with the axis of the sleeve from the opening 121, through the midsection. Moving towards the distal tip, the path of the slot 130 curves medially and then laterally, with the slot terminating at a point near, but short of, the distal tip of the sleeve. Over all, the slot has a linear portion 130a and a curved portion 130b. In effect, the partitions do not all have the same length, with at least one partition being longer than at least one partition. For instance as shown in FIG. 8, the upper half of the sleeve is longer than the lower half.

In another embodiment, shown in FIG. 11, the sleeve 104 is provided with four slots 130. The slots divide the sleeve 104 into partitions. The slots have a linear portion and a curved portion. In effect, the partitions do not all have the same length, with some of the partitions being longer than some of the other partitions.

When the pin 102 is driven to its final position, the sleeve 104 is expanded (Compare FIGS. 5, 8 to FIGS. 6, 9). As shown in FIG. 9, the curved portion of the sleeve 122 that lies between the contact points 127 is supported by the pin 102 at contact points 127. In the embodiment shown, the end 108 of the distal tip 113 is associated with this partition. This may maximize the support for the tip, thereby avoid the flexing and its potential fracture from the sleeve.

In one embodiment, the shaft 122 defines an open interior that is provided with a first zone 140 proximate the head. See FIG. 8. The first zone 140 has a first cross sectional area A—A. The open interior of the shaft is also provided with a second portion 142 proximate the distal tip that has a second cross sectional area C—C and D—D. The first cross sectional area 140 is greater than the second cross sectional area 142. In another embodiment, there is a third zone 144 positioned intermediate the first zone and second zone 140, 142, with the third zone being tapered. That is, the third zone has a varying cross sectional area that decreases incrementally over its traversal from the first zone to the second zone.

Near the distal end of the slot, there is a tapered section 144 that interfaces with the pin during expansion. As the pin is advanced, the pin enters the tapered section 144. Further advancement drives the pin through the tapered section. The cross sectional area of the pin is greater than the cross sectional area of the tapered section, thereby expanding the sleeve at section B—B. Still further advancement brings the pin in contact with the region between the taper and the distal tip 142, which also has a cross sectional area less than the cross sectional area of the pin. As the pin moves through the region between the taper and the distal tip, it encounters the curved segment of the slot. As it moves through this region 142, the partitions rest on the pin. Note that the upper partition 145 of FIG. 9 possesses an arcuate portion 146 of the curved segment. This partition 145 contacts the pin at the ends of this segment, and the distal tip itself rests on the pin. The lower partition 147 has a surface that rests on the pin.

The Bushing

Figure 10:
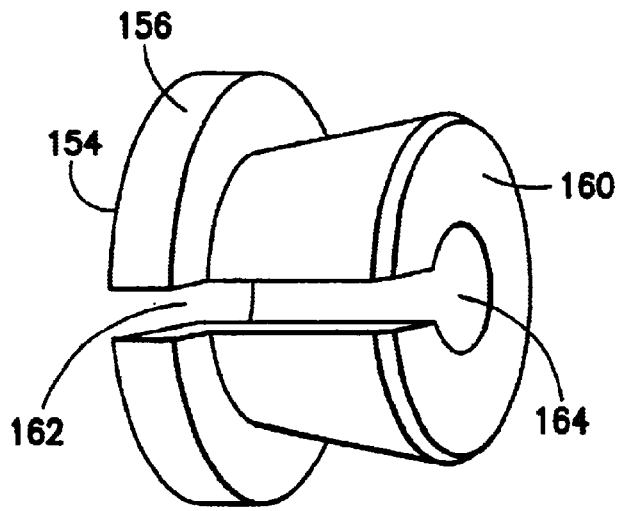
FIG. 10 is a side view of an embodiment of a bushing of the present invention.

In another embodiment of the present invention, shown in FIGS. 8, 9, and 10, a bushing 150 is employed. When deployed, the bushing resides in a cavity 152 that is located adjacent the opening 121. The cavity 152 is in communication with the opening 121 and the open interior. At its proximal end 154 the bushing is provided with flange 156 that extends outward from a tapered section 158. Tapered section 158 increases its size in a dimension as the distal end 160 is approached. A slot 162 extending in the longitudinal direction allows for compression and expansion of the bushing 150. A channel 164 extends through the bushing. The size or diameter of the channel 164 closely matches the size or diameter of the midsection 111 of the pin.

The bushing 150 is first snapped into the sleeve 104, followed by the pin 102. As the pin is pushed in, its distal end 113 expands the bushing 150 into the cavity 152. The pin 102 is further advanced until the midsection 111 passes though. The bushing 150 then reduces to its original size and shape. The bushing 164 prevents the pin 102 from falling out of the sleeve should the device be inverted during handling. If inverted, the pin 102 will drop onto the bushing 150 and be stopped by the step 115 located between its midsection 111 and distal end 113. The bushing is maintained in the cavity by the mating tapered surface within the cavity 152. In one embodiment, the bushing, sleeve, and pin come pre-assembled for the ease of the surgeon who will deploy the device within a vertebrae.

I claim:

1. An expandable sleeve deployable in a surgical implant comprised of a head, a tubular shaft defining an open interior, and a distal tip, the shaft having a length dimension and provided with a plurality of slots that divide the shaft into partitions, wherein each of the partitions has a length, and the length of the partitions are not all equal.

2. The expandable sleeve of claim 1 wherein the slots have a curved portion that extends at an angle between 0° and 90° to the length dimension of the shaft.

3. The expandable sleeve of claim 1 wherein the slots have an axial portion and a curved portion.

4. The expandable sleeve of claim 1 wherein the open interior is provided with a first zone proximate the head having a first cross sectional area and a second zone proximate the distal tip having a second cross sectional area, wherein the first cross sectional area is greater than the second cross sectional area.

5. The expandable sleeve of claim 1 wherein the slots extend from a midsection of the shaft to a terminal location on the shaft that is short of the distal tip.

6. The expandable sleeve of claim 1 further comprised of a flange extending outward from the shaft, the flange being provided with teeth that face the distal tip.

7. The expandable sleeve of claim 1 wherein the head is provided with a recess for receiving a bushing.

8. The expandable sleeve of claim 7 wherein the recess is provided with a tapered profile that varies in cross sectional area over a length dimension.

9. The expandable sleeve of claim 1 wherein the shaft is provided with slots that divide the shaft into a first slot half and a second slot half, wherein the length dimension of the first half is greater than the length dimension of the second half.

10. The expandable sleeve of claim 1 wherein the shaft is provided with slots that divide the shaft into four quarters, wherein the length dimension of two quarters is greater than the length dimension of the two other quarters.

11. The expandable sleeve of claim 1 wherein the sleeve is provided with fenestrations on an exterior side.

12. The expandable sleeve of claim 11 wherein the fenestrations are positioned near the distal tip.

13. The expandable sleeve of claim 11 wherein the fenestrations vary in their depth as measured in a radial dimension of the sleeve.

14. The expandable sleeve of claim 1 wherein when the expandable sleeve is in the expanded state, an exterior surface of the shaft along at least a portion of the length of the shaft has a thread with a thread profile substantially equal to a thread profile as defined in ASTM F 543-98.

15. An expandable sleeve deployable in a surgical implant comprised of a head, a tubular shaft defining an open interior, and a distal tip, the shaft having a length dimension and provided with a plurality of slots extending in the length dimension, the slots having an arcuate shape over at least a portion of the slot length, wherein the slots divide the shaft into partitions, and wherein the slots extend from a midsection of the shaft to a terminal location on the shaft short of the distal tip.

16. The expandable sleeve of claim 15 wherein the wherein the arcuate portion of the shaft extends at an angle between 0° and 90° to the length dimension of the shaft.

17. The expandable sleeve of claim 15 wherein the slots have a straight portion and a curved portion.

18. The expandable sleeve of claim 15 further comprised of a head engaged to the shaft at an end opposite the distal tip.

19. The expandable sleeve of claim 15 further comprised of a flange extending outward from the shaft, the flange being provided with teeth facing the distal tip.

20. The expandable sleeve of claim 15 wherein the open interior is provided with a recess for receiving a bushing.

21. The expandable sleeve of claim 20 wherein the recess is provided with a tapered profile that varies in cross sectional area over a length dimension.

22. The expandable sleeve of claim 15 wherein the sleeve is provided with fenestrations on an exterior side.

23. The expandable sleeve of claim 22 wherein the fenestrations are positioned near the distal tip.

24. The expandable sleeve of claim 22 wherein the fenestrations vary in their depth as measured in a radial dimension of the sleeve.

25. The expandable sleeve of claim 15 wherein the open interior has a first zone and a second zone that is nearest the distal tip, wherein the cross sectional area of the first zone is greater than the cross sectional area of the second zone.

26. The expandable sleeve of claim 15 wherein the shaft is provided with slots that divide the shaft into four quarters, wherein the length dimension of two quarters is greater than the length dimension of the two other quarters.

27. The expandable sleeve of claim 15 wherein when the expandable sleeve is in the expanded state, an exterior surface of the shaft along at least a portion of the length of the shaft has a thread with a thread profile substantially equal to a thread profile as defined in ASTM F 543-98.

28. A surgical implant comprised of an expandable sleeve deployable in a surgical implant comprised of a head, a tubular shaft defining an open interior, and a distal tip, the shaft having a length dimension and provided with a plurality of slots that divide the shaft into partitions, wherein each of the partitions has a length, and the length of the partitions are not all equal; and an expander pin comprised of a head and a shaft positioned within the open interior.

29. The surgical implant of claim 28 wherein the shaft of the expander pin has a distal tip and an end opposite the head, wherein the shaft is provided with a first zone proximate to the head having a first cross sectional area and a second zone proximate to the distal tip having a second cross sectional area, wherein the second cross sectional area is greater than the first cross sectional area.

30. The surgical implant of claim 28 wherein the head is provided with a recess for receiving a bushing.

31. The surgical implant of claim 28 wherein the recess is provided with a tapered profile that varies in cross sectional area over a length dimension.

32. The surgical implant of claim 28 further comprised of a bushing that resides in a cavity positioned within the open interior of the sleeve, proximate the opening of the sleeve, the bushing having a shaped portion and a flange portion extending outward of the shaped portion, the bushing further provided with a through channel dimensioned to receive the pin, and a discontinuation in the bushing, the channel being sized the same as or substantially the same as the pin, wherein the cavity is provided with dimensions complementary to the dimensions of the shaped portion to retain the shaped portion within the sleeve.

33. The surgical implant of claim 32 wherein the shaped portion has a tapered shape.

34. The surgical implant claim 32 wherein the pin is positioned within the sleeve by passing through the bushing, which expands the bushing.

35. The surgical implant of claim 32 wherein the flange portion is positioned against an abutting wall of the sleeve.

36. The surgical implant of claim 28 in an expanded state wherein the distal tip of the sleeve rests on the pin.

37. The surgical implant of claim 28 wherein when the expandable sleeve is in the expanded state, an exterior surface of the shaft along at least a portion of the length of the shaft has a thread with a thread profile substantially equal to a thread profile as defined in ASTM F 543-98.

38. The expandable sleeve of claim 28 further comprised of a flange extending outward from the shaft, the flange being provided with teeth facing the distal tip.

* * * * *